United States Patent
Suekuni et al.

(10) Patent No.: US 8,951,573 B2
(45) Date of Patent: Feb. 10, 2015

(54) DISINFECTANT COMPOSITION FOR HARD ARTICLES, AND METHOD FOR DISINFECTING OF SURFACE OF HARD ARTICLE

(75) Inventors: Tomonari Suekuni, Tokyo (JP); Takayasu Kubozono, Tokyo (JP); Kodo Horie, Tokyo (JP); Hiromu Sekioda, Osaka (JP); Tsuyoshi Miyakoshi, Osaka (JP); Yumi Kurogi, Osaka (JP)

(73) Assignee: LION Corporation (JP)

( * ) Notice: Subject to any disclaimer, the term of this patent is extended or adjusted under 35 U.S.C. 154(b) by 246 days.

(21) Appl. No.: 13/698,775

(22) PCT Filed: Apr. 18, 2011

(86) PCT No.: PCT/JP2011/059513
§ 371 (c)(1),
(2), (4) Date: Nov. 19, 2012

(87) PCT Pub. No.: WO2011/145420
PCT Pub. Date: Nov. 24, 2011

(65) Prior Publication Data
US 2013/0071488 A1  Mar. 21, 2013

(30) Foreign Application Priority Data
May 21, 2010 (JP) .................................. 2010-117393

(51) Int. Cl.
*A01N 59/20* (2006.01)
*C11D 7/18* (2006.01)
*C11D 7/10* (2006.01)
*A01N 25/22* (2006.01)
*C11D 1/722* (2006.01)
*C11D 3/04* (2006.01)
*C11D 3/33* (2006.01)
*C11D 3/48* (2006.01)
*C11D 17/06* (2006.01)
*A01N 59/00* (2006.01)
*C11D 3/39* (2006.01)

(52) U.S. Cl.
CPC ........ *A01N 25/22* (2013.01); *C11D 7/10* (2013.01); *C11D 3/3905* (2013.01); *C11D 3/3937* (2013.01); *C11D 1/722* (2013.01); *C11D 3/046* (2013.01); *C11D 3/33* (2013.01); *C11D 3/3947* (2013.01); *C11D 3/48* (2013.01); *C11D 17/06* (2013.01); *A01N 59/00* (2013.01); *A01N 59/20* (2013.01)
USPC .......................................... 424/616; 424/630

(58) Field of Classification Search
None
See application file for complete search history.

(56) References Cited

U.S. PATENT DOCUMENTS 4,902,434 A * 2/1990 Dickerson .................... 424/76.1
2003/0162685 A1 * 8/2003 Man et al. ..................... 510/445

FOREIGN PATENT DOCUMENTS

| EP | 2573159 A1 | 3/2013 |
|---|---|---|
| JP | A 2008-037885 | 2/2008 |
| JP | A-2009-148682 | 7/2009 |
| JP | A-2009-155292 | 7/2009 |
| JP | A-2009-155578 | 7/2009 |
| WO | WO 9404167 A1 * | 3/1994 |
| WO | WO 2009/078459 A1 | 6/2009 |

OTHER PUBLICATIONS

European Search Report for corresponding EP Patent Application No. 11783357.4 (mailed Nov. 5, 2013).
International Search Report for corresponding International Patent Application No. PCT/JP2011/059513 (mailed Jun. 7, 2011).

* cited by examiner

*Primary Examiner* — H. Sarah Park
(74) *Attorney, Agent, or Firm* — Merchant & Gould P.C.

(57) ABSTRACT

Disclosed are a two-agent type disinfectant composition for hard articles, which includes a first agent containing a powder mixture (A) and a second agent containing an aqueous hydrogen peroxide solution (B-1), the powder mixture (A) containing an alkali metal salt (A-1) exhibiting basicity when the salt is in the form of an aqueous solution, a water-soluble copper salt (A-2), a compound (A-3) represented by the following formula (1), and a nonionic surfactant (A-4) represented by the following formula (2), and in which the molar ratio of the water-soluble copper salt (A-2) and the compound (A-3) represented by the mixing amount of (A-3)/mixing amount of (A-2) is 3.0 to 20; and a single-agent type disinfectant composition for hard articles, which includes the components (A-1) to (A-4), and an inorganic peroxide (B-2) that releases hydrogen peroxide in water, and in which the molar ratio of the water-soluble copper salt (A-2) and the compound (A-3) represented by the mixing amount of (A-3)/mixing amount of (A-2) is 3.0 to 20. Disinfectant compositions for hard articles which have high disinfecting power against the surfaces of hard articles, have satisfactory stability of hydrogen peroxide in water, and have low foaming tendency, and a method for disinfecting the surface of a hard article by using the disinfectant composition for hard articles, can be provided.

[Chemical Formula 1]

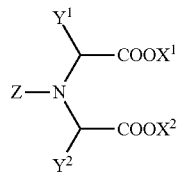

9 Claims, 1 Drawing Sheet

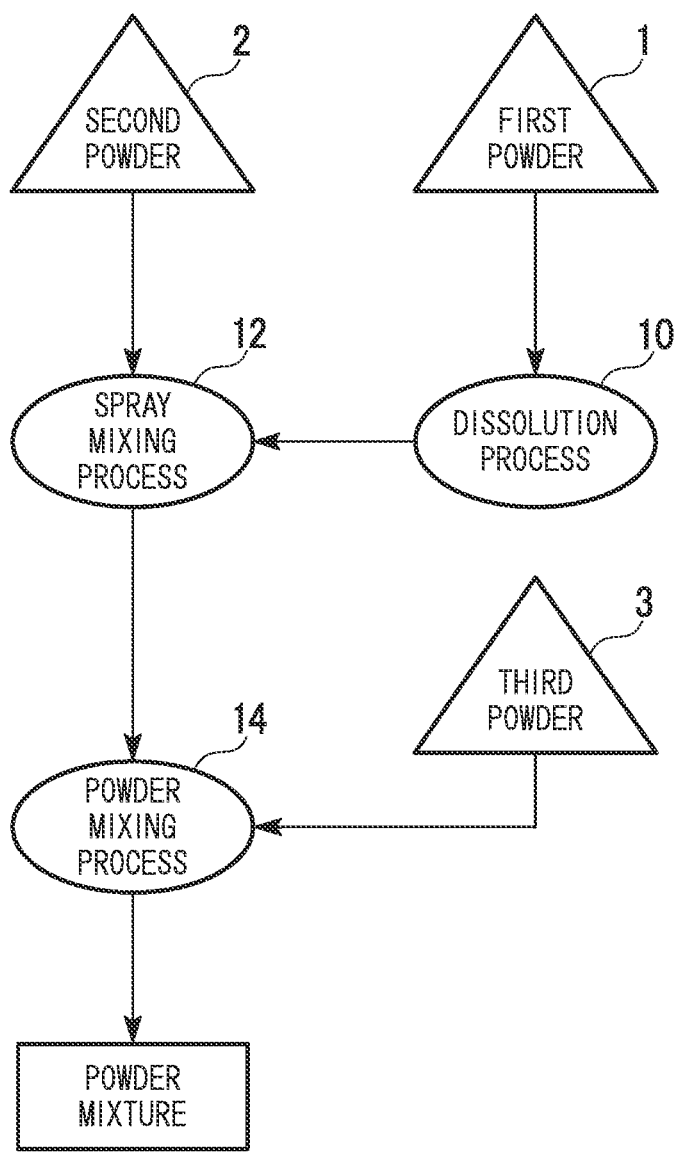

ated Japanese on 24 Nov. 2011 as WO 2011/145420.

DISINFECTANT COMPOSITION FOR HARD ARTICLES, AND METHOD FOR DISINFECTING OF SURFACE OF HARD ARTICLE

This application is a U.S. National Stage Application under 35 U.S.C. §371 of International Patent Application No. PCT/JP2011/059513, filed 18 Apr. 2011, which claims the benefit of priority to Japanese Patent Application No. 2010-117393 filed 21 May 2010, the disclosures of all of which are hereby incorporated by reference in their entireties. The International Application was published in Japanese on 24 Nov. 2011 as WO 2011/145420.

TECHNICAL FIELD

The present invention relates to a disinfectant composition for hard articles, and a method for disinfecting the surface of a hard article.

BACKGROUND

For the purpose of preventing various inconveniences caused by microorganisms and infections, it has been a conventional practice to carry out a disinfection treatment on the surfaces of hard articles (food packaging containers, beverage containers, tableware, and the like).

There are a large number of methods for the disinfection treatment method, and one of them that is known is a disinfection method of washing the aforementioned surfaces by using a disinfectant composition containing an oxidizing agent. In general, oxidizing agents lose their disinfecting power when reduced; therefore, oxidizing agents are suitable from the viewpoints of handling after use and safety.

Examples of the oxidizing agents that may be used include chlorine-based oxidizing agents such as sodium hypochlorite, ozone, and oxygen-based oxidizing agents, and as the oxygen-based oxidizing agents, hydrogen peroxide, or inorganic peroxides that generate hydrogen peroxide in water, such as sodium percarbonate, are used. In order to increase the oxidation action (disinfection action), the oxygen-based oxidizing agents are usually used in combination with alkali agents such as sodium carbonate.

Among these, methods using chlorine-based oxidizing agents may cause off-flavor and off-smell after a disinfection treatment (for example, the off-flavor and off-smell originating from a chloride of a resin that is produced when a hard surface made of a resin is treated), and methods using ozone have problems such as an increase in the capital investment due to the introduction of an ozone generator, and a risk of health hazard to the operators caused by an increase in the ozone concentration in the washing environment. Accordingly, oxygen-based oxidizing agents are preferably used for the disinfection of the surfaces of hard articles such as tableware and packaging containers.

In recent years, while the preference to hygiene is increasing, there is a strong demand for an increase in the disinfecting power of the disinfectant composition. However, oxygen-based oxidizing agents have insufficient disinfecting power even if used in combination with alkali agents, and have problems such as proliferation of microorganisms caused by the lack of disinfecting power, and consequent generation of off-flavor and off-smell. Furthermore, If the amount of the alkali agent that is used in combination is increased, there is also a problem that the alkali agent is likely to adhere to the surfaces of hard articles such as food packaging containers to be treated, or to the inside of a washing machine used for the disinfection treatment. In regard to these problems, it has been suggested to use an organic peracid precursor such as sodium 4-dodecanoyloxybenzenesulfonate, or a metal compound such as a copper salt or a manganese salt in combination, for the purpose of enhancing the disinfecting power of oxygen-based oxidizing agents.

Among these, metal compounds have a function of increasing the oxidation action of hydrogen peroxide as an oxidation catalyst and increasing the disinfecting power. However, when a metal compound is incorporated, the disinfecting power is increased, but there is a problem that hydrogen peroxide is likely to undergo hyperdegradation in water, and the residual time is short. In regard to such a problem, a method of combining a metal compound with a specific chelating agent has been suggested. For example, Patent Literature 1 suggests a combination of a specific chelating agent and a copper salt as an oxidation catalyst for disinfection and bacterial elimination. Furthermore, Patent Literature 2 suggests a composition for disinfection and bacterial elimination prepared by granulating a copper salt together with a binder compound, and mixing this with a peroxide, a specific chelating agent, an activating agent, a surfactant and the like.

CITATION LIST

Patent Literature

[Patent Literature 1] Japanese Unexamined Patent Application, First Publication No. 2009-148682
[Patent Literature 2] Japanese Unexamined Patent Application, First Publication No. 2009-155292

SUMMARY

Technical Problem

However, even if the methods described in Patent Literatures 1 and 2 and the like are used, the disinfecting power of oxygen-based oxidizing agents against the surfaces of hard articles or the stability of hydrogen peroxide in water is insufficient, and there is a demand for a further improvement. Particularly, in the case of performing a disinfection treatment at a relatively high temperature of about 50° C., hyperdegradation of hydrogen peroxide is prone to occur, and adhesion of alkali agents to the surfaces of hard articles or to the interior of a washing machine is also likely to occur. Therefore, an enhancement of the disinfecting power and an improvement of the stability of hydrogen peroxide in water become particularly important.

Furthermore, when a disinfectant composition containing a surfactant, such as the composition for disinfection and bacterial elimination described in Patent Literature 2, is applied to a washing machine, ease of foaming also causes a problem. When foaming is likely to occur, there is a problem that foam may overflow from the washing machine at the time of treatment, or rinsing may take a long time.

The present invention has been achieved under such circumstances, and it is an object of the present invention to provide disinfectant compositions for hard articles which have high disinfecting power against the surfaces of hard articles, have satisfactory stability of hydrogen peroxide in water, and have low foaming tendency, and a method for disinfecting the surface of a hard article by using the disinfectant composition for hard articles.

Solution to Problem

According to a first aspect of the present invention to solve the problems described above, there is provided a disinfectant composition for hard articles that is used for disinfection of the surfaces of hard articles containing a two-agent type disinfectant composition including a first agent containing a powder mixture (A) and a second agent containing an aqueous hydrogen peroxide solution (B-1), in which the powder mixture (A) contains an alkali metal salt (A-1) which exhibits basicity when the salt is in a form of an aqueous solution, a water-soluble copper salt (A-2), a compound (A-3) represented by the following formula (1), and a nonionic surfactant (A-4) represented by the following formula (2), and a molar ratio of the water-soluble copper salt (A-2) and the compound (A-3) represented by a mixing amount of (A-3)/mixing amount of (A-2) is 3.0 to 20.

According to a second aspect of the present invention, there is provided a disinfectant composition for hard articles that is used for the disinfection of the surfaces of hard articles containing a single-agent type disinfectant composition including an alkali metal salt (A-1) that exhibits basicity when the salt is in a form of an aqueous solution, a water-soluble copper salt (A-2), a compound (A-3) represented by the following formula (1), a nonionic surfactant (A-4) represented by the following formula (2), and an inorganic peroxide (B-2) that releases hydrogen peroxide in water, in which a molar ratio of the water-soluble copper salt (A-2) and the compound (A-3) represented by a mixing amount of (A-3)/mixing amount of (A-2) is 3.0 to 20.

[Chemical Formula 1]

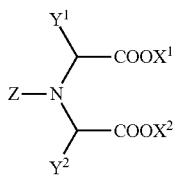
(1)

In the formula, $Y^1$ and $Y^2$ each independently represent a hydrogen atom, an alkyl group having 1 to 3 carbon atoms, $-CH_2-COOX^3$, $-CH(OH)-COOX^4$, $-CH_2CH_2-COOX^5$, $-CH_2CH_2-OH$ or $CH_2-OH$; Z represents a hydrogen atom, an alkyl group having 8 to 16 carbon atoms, $-CH_2-COOX^6$ or $CH_2CH_2-OH$; $X^1$ to $X^6$ each independently represent a hydrogen atom, an alkali metal atom, an alkaline earth metal atom, or a cationic ammonium group.

[Chemical Formula 2]

$$R^1O(EO)_p(PO)_qH \quad (2)$$

In the formula, $R^1$ represents an alkyl group or alkenyl group having 8 to 20 carbon atoms; EO represents an oxyethylene group; PO represents an oxypropylene group; p represents the average number of added moles of EO and is a number of 2 to 10; q represents the average number of added moles of PO and is a number of 1 to 2; and p>q.

According to a third aspect of the present invention, there is provided a method for disinfecting the surface of a hard article by using the disinfectant composition for hard articles of the first aspect, the disinfection method including diluting the first agent containing the powder mixture (A) with water and thereby obtaining a dilution; mixing the dilution with the second agent containing an aqueous hydrogen peroxide (B-1) solution and thereby obtaining a liquid mixture; and bringing the surface of the hard article into contact with the liquid mixture.

According to a fourth aspect of the present invention, there is provided a method for disinfecting a surface of a hard article by using the disinfectant composition for hard articles of the second aspect, the disinfection method including diluting the disinfectant composition for hard articles with water and thereby obtaining a dilution; and bringing a surface of the hard article into contact with the dilution.

In the third aspect or fourth aspect, it is preferable that the hard article be a food packaging container. Furthermore, it is preferable that the material that constitutes a surface of the hard article be glass, polycarbonate, or polyethylene terephthalate.

Advantageous Effects of Invention

According to the present invention, disinfectant compositions for hard articles, which have high disinfecting power against the surfaces of hard articles, have satisfactory stability of hydrogen peroxide in water, and have low foaming tendency, and a method for disinfecting the surface of a hard article by using the disinfectant composition for hard articles, can be provided.

BRIEF DESCRIPTION OF THE DRAWINGS

FIG. 1 is a process flow diagram illustrating the method for preparing a powder mixture of the Examples.

DETAILED DESCRIPTION

<<Disinfectant Composition for Hard Articles of First Article (Two-Agent Type)>>

The disinfectant composition for hard articles of the first aspect of the present invention (hereinafter, may be simply referred to as a disinfectant composition) is a two-agent type disinfectant composition which includes a first agent containing a powder mixture (A) described below, and a second agent containing a component (B-1) described below.

<Powder Mixture (A)>

The powder mixture (A) is a powder mixture containing a component (A-1) to a component (A-4) described below, in which the molar ratio of the component (A-2) and the component (A-3) represented by the mixing amount of (A-3)/mixing amount of (A-2) is 3.0 to 20.

[Component (A-1): Alkali Metal Salt Exhibiting Basicity when the Salt is in the Form of an Aqueous Solution]

The component (A-1) is a component which contributes to the pH adjustment of water to which the disinfectant composition has been added (treated water), an enhancement of the activity of hydrogen peroxide which is the component (B-1) (or hydrogen peroxide that is released from the component (B-2) in the second aspect described below), and a consequent enhancement of the disinfecting power. By containing the component (A-1), the pH of the treated water can be maintained to be alkaline, the activity of hydrogen peroxide in the treated water is enhanced, and the disinfecting power is enhanced.

Examples of the alkali metal in the component (A-1) include sodium, potassium, and lithium, and sodium or potassium is preferred.

As the component (A-1), inorganic salts and organic salts of alkali metals can all be used. Specific examples of the inorganic salts include carbonates, hydrogen carbonates, silicates, and hydroxides containing alkali metals as counterions. Examples of the organic salts include acetates containing alkali metals as counterions.

The component (A-1) is preferably an inorganic salt from the viewpoints of easy powder handling and satisfactory solubility in water, and is more preferably at least one selected from sodium carbonate, sodium hydrogen carbonate, and potassium carbonate.

The component (A-1) that is contained in the powder mixture (A) is such that one kind may be used, or two or more kinds may be used.

In the powder mixture (A), the mixing amount of the component (A-1) is preferably 60 to 98 mass %, and more preferably 80 to 98 mass %. When the mixing amount is greater than or equal to the lower limit or less than or equal to the upper limit of the range described above, the disinfecting power is enhanced.

[Component (A-2): Water-Soluble Copper Salt]

The component (A-2) releases copper ions in water, and the copper ions form a complex with the component (A-3) that will be described below. The complex functions as an oxidation catalyst, and enhances the disinfection effect brought about by hydrogen peroxide. This disinfection effect is effective particularly for Gram-negative bacteria (among others, *Escherichia coli*).

The "water-solubleness" of the component (A-2) means that the solubility of the substance in 100 mL of purified water at 20° C. is 1 g or greater.

Regarding the component (A-2), the type is not particularly limited as long as the compound is water-soluble, that is, the compound is capable of dissolving in water and releasing copper ions, and inorganic salts and organic salts can all be used.

Specific examples of the water-soluble copper salt that releases copper ions when dissolved in water include, as inorganic salts, copper nitrate, copper sulfate, copper chloride, copper hyperchlorate, ammonium copper chloride, and copper cyanide. Furthermore, examples of the organic salt include copper acetate, copper gluconate, copper tartrate, and copper glycine. These copper salts are such that hydrates may be used, or anhydrides may also be used.

Regarding the component (A-2), at least one selected from copper sulfate, copper chloride, copper nitrate, copper glycine and copper gluconate is preferred from the viewpoint of having satisfactory solubility in water, and copper sulfate, copper chloride and/or copper glycine is more preferred.

The component (A-2) that is included in the powder mixture (A) may be one kind, or two or more kinds may also be used.

The mixing amount of the component (A-2) in the powder mixture (A) is preferably 0.1 to 1 mass %, and more preferably 0.1 to 0.5 mass %, in terms of the anhydride. When the mixing amount is in the range described above, sufficient disinfecting power is exhibited.

[Component (A-3): Compound Represented by Formula (1)]

The component (A-3) is a compound represented by the following formula (1). The component (A-3) is such that —COOX (wherein X is any one of $X^1$ to $X^5$) is converted to —COO$^-$ by ionization in water, and this —COO$^-$ moiety forms a complex with the copper ion released from the component (A-2) as described above, thereby increasing the disinfecting power imparted by hydrogen peroxide. Furthermore, the component (A-3) also has an action of accelerating dissolution of the component (A-2) by forming a complex with copper ion.

[Chemical Formula 3]

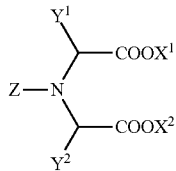

(1)

In the formula, $Y^1$ and $Y^2$ each independently represent a hydrogen atom, an alkyl group having 1 to 3 carbon atoms, —$CH_2$—$COOX^3$, —$CH(OH)$—$COOX^4$, —$CH_2CH_2$—$COOX^5$, —$CH_2CH_2$—OH or $CH_2$—OH; Z represents a hydrogen atom, an alkyl group having 8 to 16 carbon atoms, —$CH_2$—$COOX^6$ or $CH_2CH_2$—OH; and $X^1$ to $X^6$ each independently represent a hydrogen atom, an alkali metal atom, an alkaline earth metal atom, or a cationic ammonium group.

With regard to the formula (1), examples of the alkali metal atom for $X^1$ to $X^6$ include sodium and potassium.

Examples of the alkaline earth metal atom include calcium and magnesium. Meanwhile, the alkaline earth metal atom for $X^1$ to $X^6$ corresponds to a ½ atom fraction. For example, when $X^1$ is calcium, —$COOX^1$ forms "—COO$^-$½($Ca^{2+}$)".

Examples of the cationic ammonium include ammonium ($NH_4^+$); primary to tertiary ammonium ions in which one to three hydrogen atoms (H) of ammonium are substituted by organic groups; and quaternary ammonium ions in which all of H of ammonium are substituted by organic groups.

Examples of the organic group that substitutes H of ammonium include an alkanol group and an alkyl group. The number of carbon atoms of the alkanol group is preferably 1 to 3. The number of carbon atoms of the alkyl group is preferably 1 to 3. In the present specification, the alkanol group means a hydroxyalkyl group.

Specific examples of the primary to tertiary ammonium ion include cationic ions obtained by adding —H to the nitrogen atom of alkanolamines such as monoethanolamine and diethanolamine.

Specific examples of the quaternary ammonium ion include tetramethylammonium, tetraethylammonium, and tetra-n-butylammonium.

Preferred examples of the component (A-3) include the following (3a) to (3l).

(3a): a compound in which $Y^1$=H, $Y^2$=H, Z=$CH_2$—$COOX^6$, $X^1$=Na, $X^2$=Na, and $X^6$=Na (trisodium nitrilotriacetate; hereinafter, abbreviated to NTA), (3b): a compound in which $Y^1$=H, $Y^2$=$CH_3$, Z=$CH_2$—$COOX^6$, $X^1$=Na, $X^2$=Na, and $X^6$=Na (trisodium methylglycine diacetate; hereinafter abbreviated to MGDA), (3c): a compound in which $Y^1$=$CH_2$—$COOX^3$, $Y^2$=$CH_2$—$COOX^3$, Z=H, $X^1$=Na, $X^2$=Na, and $X^3$=Na (tetrasodium iminodisuccinate; hereinafter, abbreviated to IDS), (3d): a compound in which $Y^1$=$CH_2$—$COOX^3$, $Y^2$=CH(OH)—$COOX^4$, Z=H, $X^1$=Na, $X^2$=Na, $X^3$=Na, and $X^4$=Na (tetrasodium 3-hydroxy-2,2'-iminodisuccinate; hereinafter, abbreviated to HIDS), (3e): a compound in which $Y^1$=$CH_2$—$COOX^3$, $Y^2$=H, Z=$CH_2$—$COOX^6$, $X^1$=Na, $X^2$=Na, $X^3$=Na, and $X^6$=Na (tetrasodium L-aspartate-N,N-diacetate; hereinafter, abbreviated to ASDA), (3f): a compound in which $Y^1$=$CH_2CH_2$—$COOX^5$, $Y^2$=H, Z=$CH_2$—$COOX^6$, $X^1$=Na, $X^2$=Na, $X^5$=Na, and $X^6$=Na (tetrasodium glutamate-N,N-diacetate; hereinafter, abbreviated to GLDA), (3g): a compound in which $Y^1$=H, $Y^2$=H, Z=H, $X^1$=Na, and $X^2$=Na (disodium iminodiacetate; hereinafter, abbreviated to IDA), (3h): a compound in which $Y^1$=H, $Y^2$=H, Z=CH$_2$CH$_2$—OH, $X^1$=Na, and $X^2$=Na (disodium hydroxyethyliminodiacetate; hereinafter, abbreviated to HIDA), and (3i): a compound in which $Y^1$=H, $Y^2$=H, Z=an alkyl group having 12 carbon atoms, $X^1$=Na, and $X^2$=Na (disodium N-lauryliminodiacetate; hereinafter, abbreviated to C12IDA).

Among these, NTA and/or MGDA is preferred from the viewpoint of having an excellent balance between the disinfecting power and the stability of hydrogen peroxide.

The component (A-3) that is included in the powder mixture (A) is such that one kind may be used, or two or more kinds may be used.

In the powder mixture (A), the mixing amount of the component (A-3) may be any amount in which the molar ratio represented by the mixing amount of (A-3)/mixing amount of (A-2) is in a predetermined range. In view of the balance between the disinfecting power and the stability of hydrogen peroxide, the mixing amount of the component (A-3) is preferably 0.1 to 8 mass %, and more preferably 0.5 to 5 mass %, in terms of pure component.

In the powder mixture (A), the molar ratio of the component (A-2) and the component (A-3) represented by the mixing amount of (A-3)/mixing amount of (A-2) is 3.0 to 20, preferably 5.0 to 15, and more preferably 6.0 to 12. When the molar ratio is in the range described above, the balance between the disinfecting power and the stabilization of hydrogen peroxide is improved. On the other hand, if the molar ratio exceeds the upper limit of the range described above, that is, if the proportion of the component (A-3) is too high, the stability of hydrogen peroxide in the treatment liquid is satisfactory, but a sufficient disinfecting power cannot be obtained. Furthermore, if the molar ratio is less than the lower limit of the range described above, that is, if the proportion of the component (A-2) is too high, hydrogen peroxide in the treatment liquid is degraded in a short time, and disinfecting power cannot be obtained at the time of the disinfection treatment, and particularly in the later stage. In order to supplement this degradation of hydrogen peroxide, hydrogen peroxide may be additionally introduced into the treatment liquid; however, in that case, more hydrogen peroxide is used than necessary, and there is a problem in view of economic efficiency. Meanwhile, with regard to the molar ratio, the mole number of the mixing amount of (A-3) means the value calculated in terms of pure component.

[Component (A-4): Nonionic Surfactant Represented by Formula (2)]

The component (A-4) is a nonionic surfactant represented by the following formula (2).

The component (A-4) is capable of effectively effecting the disinfecting power of the disinfectant composition by increasing the wettability of the surfaces of hard articles (glass products, resin products and the like), which are the object surfaces to be disinfected. Furthermore, the component (A-4) also contributes to the dispersion of bacterial composites adhering to the object surface to be disinfection treated in the form of a so-called biofilm, or the dispersion of bacterial cells that have aggregated in a colloidal form, so that the disinfecting power is increased to a large extent. Furthermore, since the component (A-4) has low foamability, in the case of performing a disinfection treatment using the disinfectant composition on the surfaces of hard articles such as food packaging containers by using an industrial washing machine, the inconveniences caused by the generation of a large amount of foam in the washing machine (poor rinsability or overflow of foam from the washing machine, and overload in the washing water supplying pump) can be prevented.

[Chemical Formula 4]

$$R^1O(EO)_p(PO)_qH \quad (2)$$

In the formula, $R^1$ represents an alkyl group or alkenyl group having 8 to 20 carbon atoms; EO represents an oxyethylene group; PO represents an oxypropylene group; p represents the average number of added moles of EO and is a number of 2 to 10; q represents the average number of added moles of PO and is a number of 1 or 2; and p>q.

In the formula (2), the number of carbon atoms of the alkyl group or alkenyl group for $R^1$ is 8 to 20, and preferably 12 to 18. When the number of carbon atoms is less than 8, sufficient wettability to the surfaces of hard articles cannot be obtained, and therefore, disinfecting power may not be obtained. When the number of carbon atoms is greater than 20, solubility in an aqueous solution decreases, and therefore, a sufficient disinfecting power may not be exhibited.

The alkyl group or alkenyl group described above is preferably linear or branched, and is preferably a primary or secondary group.

p is 2 to 10, and has a larger value than q. When p and q satisfy the condition described above, the balance between disinfection performance and low foamability is improved. p is preferably 4 to 10.

Furthermore, the difference between p and q (p−q) is preferably 4 or greater, and more preferably 5 or greater, in view of having an excellent balance between disinfection performance and low foamability. The upper limit of p−q is 9.

The component (A-4) is such that a product produced by any known production method may be used, or a commercially available product may also be used.

The component (A-4) can be produced by, for example, using an alcohol ($R^1$OH) as a starting raw material, and adding ethylene oxide and propylene oxide to the alcohol so as to obtain the respective predetermined average number of added moles (p and q).

Regarding the alcohol, an alcohol having 8 to 20 carbon atoms is used, and a linear or branched, primary or secondary alcohol is preferred. These alcohols may be used alone or as mixtures of two or more kinds.

The method for adding ethylene oxide and propylene oxide may be random polymerization or block polymerization.

For the component (A-4) included in the powder mixture (A), one kind may be used, or two or more kinds may be used.

The mixing amount of the component (A-4) in the powder mixture (A) is preferably 0.05 to 2 mass %, more preferably 0.05 to 1.6 mass %, and even more preferably 0.1 to 1 mass %. When the mixing amount is greater than or equal to the lower limit of the range described above, the disinfecting power against the surfaces of hard articles is enhanced. When the mixing amount is less than or equal to the upper limit, there is no inconvenience such as foaming, and the usage property is enhanced.

The powder mixture (A) may also include other components in addition to the components (A-1) to (A-4) described above and the components (B-1) to (B-2) that will be described below, to the extent that the effects of the present invention are not impaired.

The other components can be appropriately selected as necessary from those known compounds as components that can be conventionally incorporated into disinfectant compositions, sterilizer compositions, bleach compositions, cleaner compositions, and the like. Specific preferred examples of the other components include a bleach activating agent, inorganic salts, organic salts, and polymer compounds that will be described below.

Bleach Activating Agent:

A bleach activating agent may be used in combination in order to increase the disinfecting power.

Examples of the bleach activating agent include sodium octanoyloxybenzenesulfonate, sodium nonanoyloxybenzenesulfonate, sodium decanoyloxybenzenesulfonate, sodium undecanoyloxybenzenesulfonate, sodium dodecanoyloxybenzenesulfonate, octanoyloxybenzoic acid, nonaoyloxybenzoic acid, decanoyloxybenzoic acid, undecanoyloxybenzoic acid, dodecanoyloxybenzoic acid, octanoyloxybenzene, nonanoyloxybenzene, decanoyloxybenzene, undecanoyloxybenzene, dodecanoyloxybenzene, and tetraacetylethylenediamine Inorganic Salts:

The inorganic salts are inorganic salts that do not correspond to the component (A-1), the component (A-2) and the component (B-2) that will be described below, and examples thereof include neutral salts such as sodium sulfate and potassium sulfate; a crystalline aluminosilicate represented by the following formula (1); an amorphous aluminosilicate represented by the following formula (II) or (III); and inorganic ammonium salts such as ammonium sulfate and ammonium chloride.

[Chemical Formula 5]

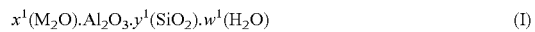

$$x^1(M_2O).Al_2O_3.y^1(SiO_2).w^1(H_2O) \quad (I)$$

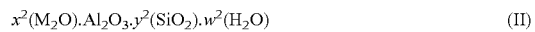

$$x^2(M_2O).Al_2O_3.y^2(SiO_2).w^2(H_2O) \quad (II)$$

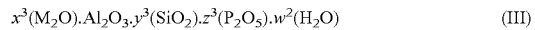

$$x^3(M_2O).Al_2O_3.y^3(SiO_2).z^3(P_2O_5).w^2(H_2O) \quad (III)$$

In the formula (1), M represents an alkali metal atom; and $x^1$, $y^1$ and $w^1$ respectively represent the mole numbers of various components ($M_2O$, $SiO_2$ and $H_2O$).

Examples of the alkali metal atom for M include sodium and potassium. $x^1$ is usually in the range of 0.7 to 1.5. $y^1$ is usually in the range of 0.8 to 6. $w^1$ is 0 or any integer.

In the formula (II), M represents an alkali metal atom; and $x^2$, $y^2$ and $w^2$ respectively represent the mole numbers of various components ($M_2O$, $SiO_2$ and $H_2O$).

Examples of the alkali metal atom for M include sodium and potassium. $x^2$ is usually in the range of 0.7 to 1.2. $y^2$ is usually in the range of 1.6 to 2.8. $w^2$ is 0 or any integer.

In the formula (III), M represents an alkali metal atom; and $x^3$, $y^3$, $z^3$ and $w^3$ respectively represent the mole numbers of various components ($M_2O$, $SiO_2$, $P_2O_5$, and $H_2O$).

Examples of the alkali metal atom for M include sodium and potassium. $x^3$ is usually in the range of 0.2 to 1.1. $y^3$ is usually in the range of 0.2 to 4.0. $z^3$ is usually in the range of 0.001 to 0.8. $w^3$ is 0 or any integer.

Organic acid Salts:

The organic salts are organic salts that do not correspond to the component (A-2) described above, and examples thereof include hydroxycarboxylates such as hydroxyacetates, tartrates, citrates and gluconates; cyclocarboxylates such as pyromellitates, benzopolycarboxylates, and cyclopentanetetracarboxylates; ether carboxylates such as carboxymethyltartronates, carboxymethyloxysuccinates, oxydisuccinates, and tartrate mono- or disuccinates; benzenesulfonates having short-chain alkyls having 1 to 5 carbon atoms, such as sodium p-toluenesulfonate, sodium xylenesulfonate, and sodium cumenesulfonate; sodium benzoate; and sodium benzenesulfonate, excluding copper salts that have copper as counterions.

Polymer Compounds:

Examples of the polymer compounds include polymers or copolymers of acrylic acid-based polymer compounds, polyacetalcarboxylates, itaconic acid, fumaric acid, tetramethylene-1,2-dicarboxylic acid, succinic acid, aspartic acid and the like; polyethylene glycol; cellulose derivatives such as carboxymethyl cellulose; polyvinylpyrrolidone and derivatives thereof; and silicone oils.

There are no particular limitations on the preparation method for the powder mixture (A), and the mixture can be prepared according to a conventional method. Specific examples include a method of dry mixing powders of the components (A-1) to (A-4) and optional components; a method of spray mixing aqueous solutions of the components (A-2) and (A-4) with the component (A-1), and then dry mixing the component (A-3) therewith; and a method of spray mixing an aqueous solution of the component (A-2) with the component (A-1), subsequently spray mixing the component (A-4) therewith, and finally dry mixing the component (A-3) therewith.

<Component (B-1): Aqueous Hydrogen Peroxide Solution>

As the component (B-1), an aqueous hydrogen peroxide solution at any concentration can be used. From the viewpoints of safety and handleability, an aqueous hydrogen peroxide solution at a hydrogen peroxide concentration of 30 to 65 mass % is preferred, and particularly, it is preferable to use an aqueous hydrogen peroxide solution at 35 mass % that is industrially prepared and merchandized.

In the disinfectant composition of the present embodiment, the component (B-1) is considered as a separate agent different from the powder mixture (A), and the mixing amount is not particularly limited. The mixing amount may be appropriately set by considering the hydrogen peroxide concentration in the aqueous hydrogen peroxide solution or the amount of the component (B-1) added to the treatment water such that the concentration in terms of pure component of hydrogen peroxide in the treatment water at the time of use reaches a value which can give a desired disinfection effect.

The disinfectant composition of the present embodiment, which contains the powder mixture (A) and the component (B-1), acquires high disinfecting power and high stability of hydrogen peroxide at the time of treatment, and can effectively disinfect microorganisms such as Gram-negative bacteria that are adhering to the surfaces of hard articles.

The reasons for obtaining the effects described above may be as follows:

(1) the component (A-1) included in the powder mixture (A) converts the pH of the treatment water to alkalinity at pH 8 to 12, and at the same time, the component (A-2) and the component (A-3) form a complex in the treatment water and function as an oxidation catalyst for hydrogen peroxide, so that the oxidation action of hydrogen peroxide is increased;

(2) the excessive degradation of hydrogen peroxide in the treatment liquid is suppressed by combining the component (A-2) and the component (A-3) at a predetermined molar ratio; and (3) the component (A-4) increases the wettability of the surfaces of hard articles, which are the object surfaces to be disinfected, and thereby the various components are efficiently brought into contact with the surfaces of hard articles, so that the disinfecting power can effectively work. Also, the component (A-4) also contributes to the dispersion of bacterial composites that are adhering to the object surfaces in the form of a so-called biofilm, or the dispersion of bacterial cells that have aggregated in a colloidal form.

Furthermore, the disinfectant composition of the present embodiment also has, in addition to the effects described above, low foaming tendency (low foamability) by containing the component (A-4) as a surfactant. This is useful when disinfection of the surfaces of hard articles is carried out with the disinfectant composition by using an industrial washing machine. That is, in the case of performing a disinfection treatment with an industrial washing machine by utilizing the oxidation action of hydrogen peroxide such as described above, solubility of the disinfectant composition and stability (length of the residual time) of hydrogen peroxide in the treatment liquid at a high temperature of about 50° C. are requested. Furthermore, when a large amount of foam is generated in the washing machine, since there are problems such as poor rinsability or overflow of foam from the washing machine, and overload of the washing water supplying pump, low foamability is also desirable. The disinfectant composition of the present embodiment satisfies such a demand.

Therefore, the disinfectant composition of the present embodiment is suitable for the use for hard articles.

Here, the hard article as used for the "surfaces of hard articles", which are the objects to be disinfected by the disinfectant composition, means an article in which at least a part of the surface is formed of a hard material. Examples of the hard material include plastics such as polycarbonate, polyethylene terephthalate, polyethylene, polypropylene, melamine resins, and acrylic resins; glass, porcelain, aluminum, iron, and stainless steel.

According to the present invention, the material that constitutes the surface of a hard article is preferably glass, polycarbonate, or polyethylene terephthalate, because on these materials, it is difficult to obtain disinfecting power with conventional cleaners due to the effect of hydrophilicity and hydrophobicity of the surface, and the present invention is highly useful.

Specific examples of the hard article include food packaging containers, beverage containers, tableware, and dental prostheses. Among these, from the viewpoint that washing is achieved by using an industrial washing machine under a high temperature environment, food packaging containers or beverage containers are preferred.

<<Method for Disinfecting Surface of Hard Article Using Disinfectant Composition (Two-Agent Type) for Hard Articles of First Embodiment>>

As the method for disinfecting the surface of a hard article by using the disinfectant composition for hard articles of the first embodiment, a method of diluting a first agent containing the powder mixture (A) with water, mixing the dilution thus obtained with a second agent containing the component (B-1), and bringing the surface of the hard article into contact with the liquid mixture thus obtained (treatment liquid), is preferred. When the first agent is diluted in advance with water before mixing with the second agent, dissolution failure or the presence or absence of undissolved residue can be checked for before use.

The amount of water used to dilute the first agent is preferably an amount which achieves a concentration of the first agent in the dilution of 1 to 10 mass %, and more preferably 3 to 8 mass %.

The second agent may be directly mixed with the dilution of the first agent, or if necessary, may be first diluted with water and then mixed. The hydrogen peroxide concentration in the second agent at the time of mixing with the dilution of the first agent is preferably 5 to 60 mass %, and more preferably 10 to 35 mass %, in terms of pure hydrogen peroxide, from the viewpoints of easy handleability and storage stability.

The mixing of the dilution of the first agent and the second agent is preferably carried out at 10 to 60° C., and more preferably at 20 to 50° C., in consideration of the stability of hydrogen peroxide.

In order to obtain sufficient disinfection performance, the concentration of hydrogen peroxide originating from the component (B-1) in the liquid mixture (treatment liquid) prepared as described above is preferably 0.01 to 0.5 mass %, and more preferably 0.05 to 0.5 mass %, in terms of pure hydrogen peroxide.

Furthermore, the concentration of the first agent in the liquid mixture (treatment liquid) is preferably 0.05 to 1 mass %, and more preferably 0.1 to 0.5 mass %, in order to obtain sufficient disinfection performance.

The pH of liquid mixture at 25° C. is preferably 8 to 12, and more preferably 9 to 11. When the pH is 8 or higher, sufficient disinfection performance can be obtained; however, if the pH is higher than 12, stability of hydrogen peroxide is degraded, and the disinfecting power may decrease.

The method for bringing the surface of a hard article into contact with the liquid mixture (treatment liquid) prepared as described above is not particularly limited. Examples thereof include a method of washing the hard article by using the liquid mixture as a cleaning liquid in a washing machine; a method of immersing the hard article in the liquid mixture; and a method of filling the liquid mixture in a trigger bottle, and spraying the liquid mixture onto the hard surface. Among these, from the viewpoint that the usefulness of the present invention is excellent, a method of washing the hard article by using a washing machine is preferred.

The temperature of the liquid mixture at the time of bringing the surface of a hard article into contact with the liquid mixture is preferably 30 to 65° C., and more preferably 40 to 55° C., when the disinfection effect, and the foaming tendency of the component (A-4) or surface wettability by the component (A-4) are taken into consideration.

<<Disinfectant Composition for Hard Articles of Second Embodiment (Single-Agent Type)>>

The disinfectant composition of the second embodiment of the present invention is a single-agent type disinfectant composition composed of a powder mixture containing the components (A-1) to (A-4) described above and a component (B-2) that will be described below, in which the molar ratio of the component (A-2) and the component (A-3) represented by the mixing amount of (A-3)/mixing amount of (A-2) is 3.0 to 20.

<Components (A-1) to (A-4)>

In regard to the disinfectant composition of the present embodiment, the components (A-1) to (A-4) may be the same substances as the components (A-1) to (A-4), respectively, described for the disinfectant composition of the first embodiment, and the molar ratio represented by (A-3)/(A-2) is also the same.

The components (A-1) to (A-4) contained in the disinfectant composition of the present embodiment are respectively such that one kind may be used, or two or more kinds may be used.

According to the present embodiment, since the disinfectant composition contains the component (B-2), when hydrogen peroxide is released from the component (B-2) in water, an "alkali metal salt exhibiting basicity when the salt is in the form of an aqueous solution" may be released at the same time. Specifically, when the component (B-2) is sodium percarbonate, hydrogen peroxide and sodium carbonate are released in water. The "alkali metal salt exhibiting basicity when the salt is in the form of an aqueous solution" released from the component (B-2) has the same function as the component (A-1). Therefore, the mixing amount of the component (A-1) in the disinfectant composition of the present embodiment is set in consideration of the type and mixing amount of the component (B-2).

Specifically, when a compound capable of releasing the "alkali metal salt exhibiting basicity when the salt is in the form of an aqueous solution" is used as the component (B-2), it is preferable to adjust the mixing amount of the component (A-1) such that the total amount of the "alkali metal salt exhibiting basicity when the salt is in the form of an aqueous solution" that may be generated from the component (A-1) and the component (B-2) would be 60 to 98 mass % relative to the total mass of the disinfectant composition.

The mixing amount of the component (A-2) in the disinfectant composition of the present embodiment is, in terms of anhydride, preferably 0.07 to 0.7 mass %, more preferably 0.07 to 0.4 mass %, and even more preferably 0.1 to 0.4 mass %, relative to the total mass of the disinfectant composition. When the mixing amount is in the range described above, sufficient disinfecting power is exhibited.

The mixing amount of the component (A-3) in the disinfectant composition of the present embodiment may be any amount in which the molar ratio represented by the mixing amount of (A-3)/mixing amount of (A-2) is in a predetermined range. From the viewpoint of the balance between the disinfecting power and the stability of hydrogen peroxide, the mixing amount is, in terms of pure component, preferably 0.07 to 5.3 mass %, more preferably 0.35 to 4.5 mass %, and even more preferably 0.9 to 4.5 mass %, relative to the total mass of the disinfectant composition.

The mixing amount of the component (A-4) in the disinfectant composition of the present embodiment is preferably 0.03 to 1.3 mass %, more preferably 0.03 to 0.7 mass %, and even more preferably 0.07 to 0.7 mass %, relative to the total mass of the disinfectant composition. When the mixing amount is greater than or equal to the lower limit of the range described above, the disinfecting power against the surfaces of hard articles is enhanced. When the mixing amount is less than or equal to the upper limit, there is no inconvenience such as foaming, and the usage property is enhanced.

<Component (B-2): Inorganic Peroxide Releasing Hydrogen Peroxide in Water>

Specific examples of the component (B-2) include hydrogen peroxide adducts of inorganic salts, such as sodium percarbonate, sodium perborate, and sodium perborate•trihydrate. Among these, from the viewpoints of solubility at the time of use and stability at the time of storage, sodium percarbonate is preferred.

Sodium percarbonate is an adduct of sodium carbonate and hydrogen peroxide, and is represented by the structural formula: $Na_2CO_3 \cdot 3/2H_2O_2$. Specifically, "PC-A" manufactured by Nippon Peroxide Co., Ltd. can be used. Furthermore, in order to further improve the stability at the time of storage as sodium percarbonate, a product coated with a coating agent on the surface (coated sodium percarbonate) may also be used. Examples of the coating agent include mixtures of silicic acid and/or a silicate and boric acid and/or a borate; and mixtures of a surfactant and an inorganic compound.

The component (B-2) contained in the disinfectant composition is such that one kind may be used, or two or more kinds may be used.

The mixing amount of the component (B-2) in the disinfectant composition is preferably 70 to 95 mass %, more preferably 80 to 95 mass %, and even more preferably 92 to 95 mass %, relative to the total mass of the disinfectant composition. When the mixing amount is greater than or equal to the lower limit, or less than or equal to the lower limit of the range described above, a sufficient disinfecting power may be obtained.

The disinfectant composition of the present embodiment may contain other components in addition to the components (A-1) to (A-4) and the components (B-1) and (B-2), to the extent that the effects of the present invention are not impaired.

The other components can be appropriately selected, as necessary, from those substances known as components that can be conventionally incorporated into disinfectant compositions, sterilizer compositions, bleach compositions, cleaner compositions, and the like. Specific preferred examples of the other components include, for example, the same bleach activating agents, inorganic salts, organic salts, and polymer compounds as those listed in the description of the first embodiment.

The disinfectant composition of the present embodiment can be prepared by mixing the components (A-1) to (A-4), component (B-2), and optional components. Specific examples of the method include a method of dry mixing powders of the components (A-1) to (A-4), the component (B-2), and optional components; a method of spray mixing aqueous solutions of the components (A-2) and (A-4) with the component (A-1), and then dry mixing the component (A-3) and the component (B-2) therewith; and a method of spray mixing an aqueous solution of the component (A-2) with the component (A-1), subsequently spray mixing the component (A-4) therewith, and then dry mixing the component (A-3) and the component (B-2) therewith.

Since the disinfectant composition of the present embodiment contains the powder mixture (A) and the component (B-2), the disinfectant composition has high disinfecting power and high stability of hydrogen peroxide at the time of treatment, and can effectively disinfect microorganisms such as Gram-negative bacteria that are adhering to the surfaces of hard articles, similarly to the disinfectant composition of the first embodiment.

Therefore, the disinfectant composition of the present embodiment is suitable for the disinfection of the surfaces of hard articles, as in the case of the disinfectant composition of the first embodiment.

<<Method for Disinfecting Surface of Hard Article by Using Disinfectant Composition for Hard Article of Second Embodiment (Single-Agent Type)>>

The method for disinfecting the surface of a hard article by using the disinfectant composition of the second embodiment may be a method of diluting the disinfectant composition with water, and bringing the surface of the hard article into contact with the dilution thus obtained.

The amount of water used is preferably an amount in which the concentration of the disinfectant composition in the dilution is 1.4 to 14 mass %, and more preferably 4.1 to 11 mass %.

Dilution of the disinfectant composition is preferably carried out at 10 to 60° C., and more preferably at 20 to 50° C., in consideration of the stability of hydrogen peroxide.

The pH of the dilution prepared as described above at 25° C. is preferably 8 to 12, and more preferably 9 to 11. When the pH is 8 or higher, sufficient disinfection performance may be obtained, but if the pH is higher than 12, stability of hydrogen peroxide is degraded, and the disinfecting power may be deteriorated.

The method for bringing the surface of a hard article into contact with the dilution (treatment liquid) prepared as described above is not particularly limited, and can be carried out in the same manner as the method for disinfecting the surface of a hard article by using the disinfectant composition for hard articles of the first embodiment (two-agent type), except that the dilution described above is used instead of the liquid mixture.

EXAMPLES

The present invention will be more specifically described with reference to Examples. However, the present invention is not intended to be limited to these Examples.

Raw materials used in the following Examples will be listed below.

[Component (A-1)]
Sodium carbonate: manufactured by Kanto Chemical Co., Inc., reagent (special grade)
Sodium hydrogen carbonate: manufactured by Kanto Chemical Co., Inc., reagent (special grade)

[Component (A-2)]
Copper sulfate pentahydrate: manufactured by Kanto Chemical Co., Inc., reagent (food additive), molecular weight 249.69 ($CuSO_4 \cdot 5H_2O$)
Copper chloride dihydrate: manufactured by Kanto Chemical Co., Inc., reagent (special grade), molecular weight 170.48 ($CuCl_2 \cdot 2H_2O$)
Copper glycine: manufactured by Advance Scientific & Chemical, Inc., reagent, molecular weight 211.66

[Component (A-3)]
MGDA: trisodium methylglycine diacetate, "Trilon M Granules" manufactured by BASF SE, molecular weight 271.11, purity 80%
NTA: trisodium nitrilotriacetate, "Trilon A92R" manufactured by BASF SE, molecular weight 257.08, purity 92%
GLDA: tetrasodium glutamate-N,N-diacetate, "Dissolvine GL-38" manufactured by Akzo Nobel N.V., molecular weight 351.13, purity 38%
IDS: tetrasodium iminodisuccinate, "Baypure CX100" manufactured by Lanxess AG, molecular weight 337.10, purity 80%
HIDA: disodium hydroxyethyliminodiacetate, "Chelest EA" manufactured by Chelest Corp., molecular weight 221.12, purity 100%

[Component (A-4)]
$C_{13}$—O-$(EO)_9(PO)_2$—H: "Lionol TDM-90" manufactured by Lion Corp. In the formula, "$C_{13}$" represents an alkyl group or alkenyl group having 13 carbon atoms.
$C_{palm}$—O-$(EO)_7(PO)_2$—H: "Leox 2008C" manufactured by Lion Corp. "$C_{palm}$" represents an alkyl group or alkenyl group containing about 12 carbon atoms on average that is contained in the higher alcohols derived from natural palm oil.
$C_{13}$—O-$(EO)_5(PO)_1$—H: "Lionol TDL-50" manufactured by Lion Corp. In the formula, "$C_{13}$" represents an alkyl group or alkenyl group having 13 carbon atoms.

[Component (A-4')]
$C_{12,14}$—O-$(EO)_3(PO)_3$—H: a product obtained by adding 3 molar equivalents of ethylene oxide and 3 molar equivalents of propylene oxide by random copolymerization to natural alcohol CO-1214 (mixture of C12 alcohols and C14 alcohols) manufactured by Procter & Gamble, Co. In the formula, "$C_{12,14}$" represents an alkyl group or alkenyl group having 12 or 14 carbon atoms.
$C_{13}$—O-$(EO)_7(PO)_3$—H: "Lionol TD-730" manufactured by Lion Corp. In the formula, "$C_{13}$" represents an alkyl group or alkenyl group having 13 carbon atoms.
Sucrose fatty acid ester: "Ryoto Sugar Ester P-1570" manufactured by Mitsubishi-Kagaku Foods Corp.
$C_{12,14}$—O-$(EO)_{15}$—H: a product obtained by adding 15 molar equivalents of ethylene oxide to natural alcohol CO-1214 manufactured by Procter & Gamble, Co. In the formula, "$C_{12,14}$" represents an alkyl group or alkenyl group having 12 or 14 carbon atoms.

[Optional Components]
Sodium sulfate: manufactured by Kanto Chemical Co., Ltd., reagent (special grade)

[Component (B-1) and Component (B-2)]
Hydrogen peroxide: 35% aqueous hydrogen peroxide, manufactured by Kanto Chemical Co., Ltd.
Sodium percarbonate: "PC-A" (containing 67.5% of sodium carbonate component and 32.5% of hydrogen peroxide component) manufactured by Nippon Peroxide Co., Ltd.

Examples 1 to 14 and Comparative Examples 1 to 10

Two-Agent Type

Powder mixtures of the various Examples were prepared by the following procedure, according to the preparation method illustrated in the process flow diagram of FIG. 1, in accordance with the compositions indicated in Tables 1 and 2 so as to obtain a total mass of 56 kg each. Meanwhile, the values of the respective components in the tables represent percentage by mass (mass %), and the symbol "-" indicates that the sample was not evaluated.

As a first powder 1, the component (A-2) and the component (A-4) were dissolved in purified water, and thus an aqueous metal solution was prepared (dissolution process 10).

Subsequently, the component (A-1) was introduced as a second powder 2 into a horizontal cylindrical mixing drum (internal volume: 130 L, diameter: 0.6 m), and the powder was stirred for 2 minutes at a speed of rotation of 20 rpm (Fr=0.14). Thereafter, the aqueous metal solution was mixed with the powder by spraying (liquid droplet size: 20 μm to 50 μm) the aqueous metal solution at a spraying rate of 100 mL/min by using a two-flow nozzle (manufactured by H. Ikeuchi Co., Ltd.: SETO0407, spray pressure: 1.2 kg/cm$^2$) (spray mixing process 12). The liquid droplet size was measured by using a laser light scattering particle size distribution analyzer (Mastersizer S manufactured by Malvern Instruments, Ltd.).

After completion of spraying, the component (A-3) was introduced as a third powder 3 into the horizontal cylindrical mixing drum, and the contents were mixed for 5 minutes at a speed of rotation of 20 rpm. Thus, a powder mixture (A) of each Example was prepared (powder mixing process 14).

The following evaluations and tests were carried out by using the powder mixtures thus obtained (first agents of two-agent type disinfectant compositions). Among these, the foaming power evaluation was carried out by using only the powder composition (A) (first agent); and the initial disinfecting power evaluation, the hydrogen peroxide persistence evaluation, and the actual machine disinfection test were carried out by mixing the powder composition (A) (first agent) that had been diluted in advance with water, and an aqueous hydrogen peroxide solution (second agent). However, only in Comparative Example 4, these evaluations and tests were carried out without mixing the powder composition with an aqueous hydrogen peroxide solution. The results are indicated in Tables 1 and 2.

[Foaming Power Evaluation (Foam Volume Measurement)]

0.2 g of the powder mixture (A) was weighed, and ion-exchanged water was added to make the total amount 100 g.

20 mL of this solution was collected and transferred into a graded colorimetric tube having a capacity of 100 mL, and the temperature of the solution was adjusted to 50° C. in a warm bath. This colorimetric tube was shaken vertically for 20 seconds at a speed of 2 reciprocations/second, and then the tube was left to stand for 30 seconds. After being left to stand, the volume of foam (foam volume) present above the liquid surface was measured by visual inspection. A smaller value of this foam volume indicates lower foaming power.

Meanwhile, if a foaming power with a foam volume of 10 mL or less was obtained in the present evaluation, when the disinfectant composition was supplied to washing in a bottle washing machine in the actual machine disinfection test that will be described below, the disinfectant composition could be used without the problem of poor rinsability or overflow of foam from the washing machine.

[Initial Disinfecting Power Evaluation]

0.4 g of the powder mixture (A) as the first agent was weighed, and the powder mixture was dissolved in sterile water to make the total amount 100 g. 5 mL of this solution was collected into a test tube, and the temperature of this solution was adjusted to 50° C. in a warm bath. To this solution, 0.025 mL (about 0.028 g) of the component (B-1) (35% aqueous hydrogen peroxide solution) as the second agent was added (not added only in Comparative Example 4), and then the remainder was adjusted with sterile water to obtain a total volume of 9.9 mL. To this, 0.1 mL of an *Escherichia coli* stock solution (NBRC12732, name of organization: Incorporated Administrative Agency National Institute of Technology and Evaluation, Biological Resource Center) that had been adjusted to contain $1 \times 10^6$ cells/mL was added to prepare a test liquid, and this test liquid was uniformly stirred for 15 seconds. Subsequently, 1 mL of the test liquid was collected and added to 9 mL of SCDLP medium (Soybean-Casein Digest Broth with Lectin & Polysorbate 80: manufactured by Wako Pure Chemical Industries, Ltd.) to obtain a 10-fold dilution. An operation of further diluting the dilution thus obtained 10 times was repeated two times, and thus dilutions ranging from a 10-fold dilution to a 1000-fold dilution were obtained. 1.0 mL of each was collected from these dilutions into Petri dishes, and about 15 mL of dissolved standard agar medium (manufactured by Wako Pure Chemical Industries, Ltd.) was added to each of the Petri dishes. The mixtures were homogenized and cultured at 37° C. for 2 days, and then samples with a colony number in the range of 30 to 300 were selected. The colony number was counted, and the number of surviving cells was determined Based on the difference between the logarithmic value of the initial number of cells ($1 \times 10^6$ cells/mL) and the logarithmic value of the number of surviving cells after the test ($\Delta$Log), the evaluation was carried out according to the following evaluation criteria.

(Evaluation Criteria)

A: $\Delta$Log value is 3 or greater.
B: $\Delta$Log value is greater than or equal to 2 and less than 3.
C: $\Delta$Log value is greater than or equal to 1 and less than 2.
D: $\Delta$Log value is less than 1.

[Hydrogen Peroxide Persistence Evaluation]

Into a stainless steel beaker having a volume of 2 L, 1.6 g of the powder mixture (A) as the first agent was weighed, and 800 mL of tap water was added thereto. The mixture was dissolved under stirring, and then was heated to 50° C. in a warm bath. To this, 16 mL (18.1 g) of the component (B-1) (35% aqueous hydrogen peroxide solution) as the second agent was added, and stirring was initiated again. After stirring for 1 hour, about 3 mL of the solution was collected, the volume was adjusted to 200 mL with ion-exchanged water, and then the entire amount was transferred to a 300-mL conical flask. 10 mL of sulfuric acid at 2 mol/L was added thereto, and it was confirmed by using a pH meter that the pH was 4 or lower. The hydrogen peroxide concentration was determined by an iodometry method of titrating the solution with 0.02 mol/L potassium permanganate until light coloration was achieved. Based on the results, the hydrogen peroxide residual ratio (%) was calculated by the formula: [hydrogen peroxide concentration after stirring for 1 hour/initial hydrogen peroxide concentration]$\times 100$, and the hydrogen peroxide persistence was evaluated according to the following evaluation criteria.

The initial hydrogen peroxide concentration was a value obtained by measuring the hydrogen peroxide concentration immediately after adding the component (B-1) and initiating stirring, by means of the iodometry method described above.

(Evaluation Criteria)

A: The hydrogen peroxide residual ratio is 30% or higher.
B: The hydrogen peroxide residual ratio is greater than or equal to 10 and less than 30%.
D: The hydrogen peroxide residual ratio is less than 10%.

[Actual Machine Disinfection Test]

76 L of tap water was introduced into a washing water tank for a washing machine for bottles (manufactured by Norland International, Inc., BW150). 160 g of the powder mixture (A) as the first agent was dissolved under stirring by using 4 L of tap water, and the solution was introduced into the washing water tank. Subsequently, the washing water was heated so that the washing water temperature would be 50 to 55° C. To this, 0.6 L of the component (B-1) (35% aqueous hydrogen peroxide solution) as the second agent was introduced, and polycarbonate bottles (capacity 12 L) that had been used for drinking water use and collected were sequentially washed (15 seconds$\times$3 times) and rinsed (15 seconds$\times$3 times). Thus, 120 bottles in total were subjected to a disinfection treatment.

100 mL of sterile water was added to each set of 10 bottles that had been disinfection treated, and then the bottles were stoppered with sterilized caps. The bottles were vertically shaken vigorously for 1 minute, and bacteria in the bottles were extracted. The entire amount of this bacteria extract was filtered through a sterilized membrane filter, and then this membrane filter was transferred onto a standard agar medium plate and cultured for 2 days at 37° C. The total number of bacteria in each set of 10 bottles was evaluated as the number of residual bacteria.

When the number of residual bacteria was found to be less than 10 in total in the present test, it was evaluated that a sufficient disinfecting power was obtained.

TABLE 1

| | | Example | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| (A) First agent | (A-1) Sodium carbonate | 95.60 | 94.15 | 97.05 | 95.60 | 95.60 | 95.60 | 95.60 | 95.60 | 95.60 | 95.60 | 80.60 | 80.60 | 80.90 | 79.35 |
| | Sodium hydrogen carbonate | | | | | | | | | | | | | 15.00 | 15.00 |
| | (A-2) *1 Copper sulfate pentahydrate | 0.30 (0.19) | 0.20 (0.13) | 0.50 (0.32) | | | 0.30 (0.19) | 0.30 (0.19) | 0.30 (0.19) | 0.30 (0.19) | 0.30 (0.19) | 0.30 (0.19) | 0.30 (0.19) | 0.30 (0.19) | 0.30 (0.19) |
| | Copper chloride dihydrate | | | | 0.30 (0.24) | | | | | | | | | | |
| | Copper glycine | | | | | 0.30 | | | | | | | | | |
| | (A-3) *2 MGDA | 3.75 (3.00) | 5.30 (4.24) | 2.10 (1.68) | 3.75 (3.00) | 3.75 (3.00) | | | | | 3.75 (3.00) | 3.75 (3.00) | 3.75 (3.00) | 3.75 (3.00) | 3.75 (3.00) |
| | NTA | | | | | | 3.75 (3.45) | | | | | | | | |
| | GLDA | | | | | | | 3.75 (1.43) | | | | | | | |
| | IDS | | | | | | | | 3.75 (3.00) | | | | | | |
| | HIDA | | | | | | | | | 3.75 (3.75) | | | | | |
| | (A-4) C₁₃—O—(EO)₉(PO)₂—H | 0.35 | 0.35 | 0.35 | 0.35 | 0.35 | 0.35 | 0.35 | 0.35 | 0.35 | | | | | |
| | C_palm—O—(EO)₄(PO)₂—H | | | | | | | | | | 0.35 | | | | |
| | C₁₃—O—(EO)₅(PO)₁—H | | | | | | | | | | | 0.35 | | | |
| | C₁₂,₁₄—O—(EO)₃(PO)₃—H | | | | | | | | | | | | 0.25 | | |
| | C₁₃—O—(EO)₃(PO)₃—H | | | | | | | | | | | | 0.10 | 0.05 | 1.60 |
| | (A-4') Sucrose fatty acid esters | | | | | | | | | | | | | | |
| | C₁₂,₁₄—O—(EO)₁₅—H | | | | | | | | | | | | | | |
| | Optional component Sodium sulfate | | | | | | | | | | | 15.00 | | | |
| | Total | 100 | 100 | 100 | 100 | 100 | 100 | 100 | 100 | 100 | 100 | 100 | 100 | 100 | 100 |
| | (A-3)/(A-2) molar ratio | 9.2 | 19.5 | 3.1 | 6.3 | 7.8 | 10.6 | 3.4 | 7.4 | 9.3 | 9.2 | 9.2 | 9.2 | 9.2 | 9.2 |
| (B-1) Second agent | 35% aqueous hydrogen peroxide solution *3 | 100 (35) | 100 (35) | 100 (35) | 100 (35) | 100 (35) | 100 (35) | 100 (35) | 100 (35) | 100 (35) | 100 (35) | 100 (35) | 100 (35) | 100 (35) | 100 (35) |
| | Total | 100 | 100 | 100 | 100 | 100 | 100 | 100 | 100 | 100 | 100 | 100 | 100 | 100 | 100 |
| Evaluation ((A) only) | Foam volume (mL) | 5 | 5 | 5 | 5 | 5 | 5 | 5 | 5 | 5 | 4 | 2 | 6 | 2 | 9 |
| Evaluation (Mixture) | Initial disinfecting power evaluation | A | B | A | A | A | B | A | A | B | A | A | B | A | A |
| | Hydrogen peroxide persistence test | A | A | B | A | A | A | B | B | A | A | A | A | A | A |
| | Actual machine disinfection test (number of residual bacteria) | 2 | 6 | 4 | 3 | 2 | 9 | 8 | 8 | 6 | 3 | 6 | 7 | 9 | 4 |

TABLE 2

|  |  |  | Comparative Example 1 | Comparative Example 2 | Comparative Example 3 | Comparative Example 4 | Comparative Example 5 |
|---|---|---|---|---|---|---|---|
| (A) First agent | (A-1) | Sodium carbonate Sodium hydrogen carbonate | 95.90 | 99.35 | 95.95 | 95.60 | 90.95 |
|  | (A-2) *1 | Copper sulfate pentahydrate Copper chloride dihydrate Copper glycine |  | 0.30 (0.19) | 0.30 (0.19) | 0.30 (0.19) | 0.30 (0.19) |
|  | (A-3) *2 | MGDA | 3.75 (3.00) |  | 3.75 (3.00) | 3.75 (3.00) | 8.40 (6.72) |
|  | (A-4) | $C_{13}$—O—$(EO)_9(PO)_2$—H $C_{palm}$—O—$(EO)_7(PO)_2$—H $C_{13}$—O—$(EO)_5(PO)_1$—H | 0.35 | 0.35 |  | 0.35 | 0.35 |
|  | (A-4') | $C_{12,14}$—O—$(EO)_3(PO)_3$—H $C_{13}$—O—$(EO)_7(PO)_3$—H Sucrose fatty acid esters $C_{12,14}$—O—$(EO)_{15}$—H |  |  |  |  |  |
|  | Optional component | Sodium sulfate |  |  |  |  |  |
|  |  | Total | 100 | 100 | 100 | 100 | 100 |
|  |  | (A-3)/(A-2) molar ratio | — | 0.0 | 9.2 | 9.2 | 20.6 |
| (B-1) Second agent | | 35% aqueous hydrogen peroxide solution *3 | 100 (35) | 100 (35) | 100 (35) |  | 100 (35) |
|  |  | Total | 100 | 100 | 100 | 0 | 100 |
| Evaluation ((A) only) |  | Foam volume (mL) | 5 | 5 | 1 | 5 | 5 |
| Evaluation (Mixture) |  | Initial disinfecting power evaluation | D | A | C | D | C |
|  |  | Hydrogen peroxide persistence test | A | D | A | — | A |
|  |  | Actual machine disinfection test (number of residual bacteria) | 135 | 109 | 58 | 516 | 122 |

|  |  |  | Comparative Example 6 | Comparative Example 7 | Comparative Example 8 | Comparative Example 9 | Comparative Example 10 |
|---|---|---|---|---|---|---|---|
| (A) First agent | (A-1) | Sodium carbonate Sodium hydrogen carbonate | 98.15 | 95.60 | 95.60 | 95.60 | 95.60 |
|  | (A-2) *1 | Copper sulfate pentahydrate Copper chloride dihydrate Copper glycine | 0.30 (0.19) | 0.30 (0.19) | 0.30 (0.19) | 0.30 (0.19) | 0.30 (0.19) |
|  | (A-3) *2 | MGDA | 1.20 (0.96) | 3.75 (3.00) | 3.75 (3.00) | 3.75 (3.00) | 3.75 (3.00) |
|  | (A-4) | $C_{13}$—O—$(EO)_9(PO)_2$—H $C_{palm}$—O—$(EO)_7(PO)_2$—H $C_{13}$—O—$(EO)_5(PO)_1$—H | 0.35 |  |  |  |  |
|  | (A-4') | $C_{12,14}$—O—$(EO)_3(PO)_3$—H $C_{13}$—O—$(EO)_7(PO)_3$—H Sucrose fatty acid esters $C_{12,14}$—O—$(EO)_{15}$—H |  | 0.35 | 0.35 | 0.35 | 0.35 |
|  | Optional component | Sodium sulfate |  |  |  |  |  |
|  |  | Total | 100 | 100 | 100 | 100 | 100 |
|  |  | (A-3)/(A-2) molar ratio | 2.9 | 9.2 | 9.2 | 9.2 | 9.2 |
| (B-1) Second agent | | 35% aqueous hydrogen peroxide solution *3 | 100 (35) | 100 (35) | 100 (35) | 100 (35) | 100 (35) |
|  |  | Total | 100 | 100 | 100 | 100 | 100 |
| Evaluation ((A) only) |  | Foam volume (mL) | 5 | 1 | 2 | 4 | 35 |
| Evaluation (Mixture) |  | Initial disinfecting power evaluation | A | C | C | C | A |
|  |  | Hydrogen peroxide persistence test | D | A | A | D | A |
|  |  | Actual machine disinfection test (number of residual bacteria) | 74 | 21 | 20 | 92 | — |

*1: In Table 1 and Table 2, the number in the parentheses for the component (A-2) represents the amount in terms of anhydride.
*2: In Table 1 and Table 2, the number in the parentheses for the component (A-3) represents the amount in terms of the pure component.
*3: In Table 1 and Table 2, the number in the parentheses for the component (B-1) represents the amount of pure hydrogen peroxide.

As shown in Tables 1 and 2, Examples 1 to 14 all had a foam volume of 10 mL or less, and satisfactory results were obtained in all the evaluations of the initial disinfecting power evaluation, the hydrogen peroxide persistence evaluation and the actual machine disinfection test.

On the other hand, in Comparative Example 1 in which the component (A-2) was not incorporated, Comparative Example 3 in which the component (A-4) was not incorporated, Comparative Example 4 in which the component (B-1) was not incorporated, and Comparative Example 5 in which the molar ratio of the mixing ratio of the mixing amount of (A-3)/mixing amount of (A-2) was 20.6, the evaluation results for the initial disinfecting power evaluation and the actual machine disinfection test were all poor.

In Comparative Example 2 in which the component (A-3) was not incorporated, Comparative Example 6 in which the molar ratio of the mixing amount of (A-3)/mixing amount of (A-2) was 2.9, and Comparative Example 9 in which a sucrose fatty acid ester was incorporated instead of the component (A-4), the results of the hydrogen peroxide persistence evaluation and the actual machine disinfection test were poor. Particularly, in Comparative Example 9, the initial disinfecting power evaluation results were also poor. It is speculated that the actual machine disinfection test results were poor because hydrogen peroxide was degraded in a short time in the washing machine for bottles.

In Comparative Examples 7 and 8 in which $C_{12,14}$—O—$(EO)_3(PO)_3$—H or $C_{13}$—O—$(EO)_7(PO)_3$—H was incorporated instead of the component (A-4), the initial disinfecting power evaluation results and the actual machine disinfection test results were all poor.

In Comparative Example 10 in which $C_{12,14}$-$(EO)_{15}$—H was incorporated instead of the component (A-4), the foaming power was high, and when the disinfectant composition was supplied to the washing in a bottle washing machine in the actual machine disinfection test, foam overflow from the washing machine occurred, while rinsability was also poor.

Examples 15 to 28 and Comparative Examples 11 to 19

Single-Agent Type

Powder mixtures of the various Examples were prepared by the following procedure, according to the preparation method illustrated in the process flow diagram of FIG. 1, in accordance with the compositions indicated in Tables 3 and 4 so as to obtain a total mass of 56 kg each. Meanwhile, the values of the respective components in the tables represent percentage by mass (mass %), and the symbol "-" indicates that the sample was not evaluated.

As a first powder 1, the component (A-2) and the component (A-4) were dissolved in purified water, and thus an aqueous metal solution was prepared (dissolution process 10).

Subsequently, the component (A-1) was introduced as a second powder 2 into a horizontal cylindrical mixing drum (internal volume: 130 L, diameter: 0.6 m), and the powder was stirred for 2 minutes at a speed of rotation of 20 rpm (Fr=0.14). Thereafter, the aqueous metal solution was mixed with the powder by spraying (liquid droplet size: 20 μm to 50 μm) the aqueous metal solution at a spraying rate of 100 mL/min by using a two-flow nozzle (manufactured by H. Ikeuchi Co., Ltd.: SETO0407, spray pressure: 1.2 kg/cm$^2$) (spray mixing process 12). The liquid droplet size was measured by using a laser light scattering particle size distribution analyzer (Mastersizer S manufactured by Malvern Instruments, Ltd.).

After completion of spraying, the component (A-3) and component (B-2) were introduced as a third powder 3 into the horizontal cylindrical mixing drum, and the contents were mixed for 5 minutes at a speed of rotation of 20 rpm. Thus, a powder mixture of each Example was prepared (powder mixing process 14).

The following evaluations and tests were carried out by using the powder mixtures thus obtained (single-agent type disinfectant compositions). The results are indicated in Tables 3 and 4.

[Foaming Power Evaluation (Foam Volume Measurement)]

0.3 g of the disinfectant composition was weighed, and ion-exchanged water was added to make the total amount 100 g. 20 mL of this solution was collected and transferred into a graded colorimetric tube having a capacity of 100 mL, and the temperature of the solution was adjusted to 50° C. in a warm bath. This colorimetric tube was shaken vertically for 20 seconds at a speed of 2 reciprocations/second, and then the tube was left to stand for 30 seconds. After being left to stand, the volume of foam (foam volume) present above the liquid surface was measured by visual inspection. A smaller value of this foam volume indicates lower foaming power.

Meanwhile, if a foaming power with a foam volume of 10 mL or less was obtained in the present evaluation, when the disinfectant composition was supplied to washing in a bottle washing machine in the actual machine disinfection test that will be described below, the disinfectant composition could be used without the problem of poor rinsability or overflow of foam from the washing machine.

[Initial Disinfecting Power Evaluation]

0.6 g of the disinfectant composition was weighed, and the powder mixture was dissolved in sterile water to make the total amount 100 g. 5 mL of this solution was collected into a test tube, and the temperature of this solution was adjusted to 50° C. in a warm bath. The remainder was adjusted with sterile water such that the total volume of this solution would be 9.9 mL. To this, 0.1 mL of an *Escherichia coli* stock solution (NBRC12732, name of organization: Incorporated Administrative Agency National Institute of Technology and Evaluation, Biological Resource Center) that had been adjusted to contain $1 \times 10^6$ cells/mL was added to prepare a test liquid, and this test liquid was uniformly stirred for 15 seconds. Subsequently, 1 mL of the test liquid was collected and added to 9 mL of SCDLP medium (Soybean-Casein Digest Broth with Lectin & Polysorbate 80: manufactured by Wako Pure Chemical Industries, Ltd.) to obtain a 10-fold dilution. An operation of further diluting the dilution thus obtained 10 times was repeated two times, and thus dilutions ranging from a 10-fold dilution to a 1000-fold dilution were obtained. 1.0 mL each was collected from these dilutions into Petri dishes, and about 15 mL of dissolved standard agar medium (manufactured by Wako Pure Chemical Industries, Ltd.) was added to each of the Petri dishes. The mixtures were homogenized and cultured at 37° C. for 2 days, and then samples with a colony number in the range of 30 to 300 were selected. The colony number was counted, and the number of surviving cells was determined. Based on the difference between the logarithmic value of the initial number of cells ($1 \times 10^6$ cells/mL) and the logarithmic value of the number of surviving cells after the test (ΔLog), the evaluation was carried out according to the following evaluation criteria.

(Evaluation Criteria)
A: ΔLog value is 3 or greater.
B: ΔLog value is greater than or equal to 2 and less than 3.
C: ΔLog value is greater than or equal to 1 and less than 2.
D: ΔLog value is less than 1.

[Hydrogen Peroxide Persistence Evaluation]

In a stainless steel beaker having a volume of 2 L, 2.4 g of the disinfectant composition was weighed, and 800 mL of tap water that had been heated to 50° C. in advance in a warm bath was added thereto. The mixture was dissolved under stirring. After stirring for 1 hour, about 3 mL of the solution was collected, the volume was adjusted to 200 mL with ion-exchanged water, and then the entire amount was transferred to a 300-mL conical flask. 10 mL of sulfuric acid at 2 mol/L was added thereto, and it was confirmed by using a pH meter that the pH was 4 or lower. The hydrogen peroxide concentration was determined by an iodometry method of titrating the solution with 0.02 mol/L potassium permanganate until light staining was achieved. Based on the results, the hydrogen peroxide residual ratio (%) was calculated by the formula: [hydrogen peroxide concentration after stirring for 1 hour/initial hydrogen peroxide concentration]×100, and the hydrogen peroxide persistence was evaluated according to the following evaluation criteria.

The initial hydrogen peroxide concentration was a value obtained by measuring the hydrogen peroxide concentration immediately after adding the component (B-1) and initiating stirring, by means of the iodometry method described above.

(Evaluation Criteria)
A: The hydrogen peroxide residual ratio is 30% or higher.
B: The hydrogen peroxide residual ratio is greater than or equal to 10 and less than 30%.
D: The hydrogen peroxide residual ratio is less than 10%.

[Actual Machine Disinfection Test]

76 L of tap water was introduced into a washing water tank for a washing machine for bottles (manufactured by Norland International, Inc., BW150), and then the tap water was heated to 50° C. to 55° C. 240 g of the disinfectant composition was dissolved under stirring by using 10 L of tap water, and then the solution was introduced into the washing water tank. Polycarbonate bottles (capacity 12 L) that had been used for drinking water use and collected were sequentially washed (15 seconds×3 times) and rinsed (15 seconds×3 times). Thus, 120 bottles in total were subjected to a disinfection treatment.

100 mL of sterile water was added to each set of 10 bottles that had been disinfection treated, and then the bottles were stoppered with sterilized caps. The bottles were vertically shaken vigorously for 1 minute, and bacteria in the bottles were extracted. The entire amount of this bacteria extract was filtered through a sterilized membrane filter, and then this membrane filter was transferred onto a standard agar medium plate and cultured for 2 days at 37° C. The total number of bacteria in each set of 10 bottles was evaluated as the number of residual bacteria.

When the number of residual bacteria was found to be less than 10 in total in the present test, it was evaluated that a sufficient disinfecting power was obtained.

TABLE 3

| | | Example | | | | | | |
|---|---|---|---|---|---|---|---|---|
| | | 15 | 16 | 17 | 18 | 19 | 20 | 21 |
| (A-1) | Sodium carbonate | 5.05 | 2.15 | 4.65 | 4.05 | 5.05 | 5.05 | 5.05 |
| | Sodium hydrogen carbonate | | | | | | | |
| (A-2) *4 | Copper sulfate pentahydrate | 0.20 (0.13) | 0.20 (0.13) | 0.60 (0.38) | | | 0.20 (0.13) | 0.20 (0.13) |
| | Copper chloride dihydrate | | | | 0.20 (0.16) | | | |
| | Copper glycine | | | | | 0.20 | | |
| (A-3) *5 | MGDA | 2.50 (2.00) | 5.40 (4.32) | 2.50 (2.00) | 3.50 (2.80) | 2.50 (2.00) | | |
| | NTA | | | | | | 2.50 (2.30) | |
| | GLDA | | | | | | | 2.50 (0.95) |
| | IDS | | | | | | | |
| | HIDA | | | | | | | |
| (A-4) | $C_{13}$—O—$(EO)_9(PO)_2$—H | 0.25 | 0.25 | 0.25 | 0.25 | 0.25 | 0.25 | 0.25 |
| | $C_{palm}$—O—$(EO)_7(PO)_2$—H | | | | | | | |
| | $C_{13}$—O—$(EO)_5(PO)_1$—H | | | | | | | |
| (B-2) | Sodium percarbonate | 92.00 | 92.00 | 92.00 | 92.00 | 92.00 | 92.00 | 92.00 |
| | (in the content of sodium carbonate) | (62.10) | (62.10) | (62.10) | (62.10) | (62.10) | (62.10) | (62.10) |
| | (in the content of hydrogen peroxide) | (29.90) | (29.90) | (29.90) | (29.90) | (29.90) | (29.90) | (29.90) |
| Optional component | Sodium sulfate | | | | | | | |
| Total | | 100 | 100 | 100 | 100 | 100 | 100 | 100 |
| (A-3)/(A-2) molar ratio | | 9.2 | 19.9 | 3.1 | 8.8 | 7.8 | 11.2 | 3.4 |
| Evaluation | Foam volume (mL) | 5 | 5 | 5 | 5 | 5 | 5 | 5 |
| | Disinfecting power test | A | B | A | A | A | B | A |
| | Hydrogen peroxide residual ratio | A | A | B | A | A | A | B |
| | Actual machine disinfection test (number of residual bacteria) | 3 | 7 | 5 | 4 | 2 | 6 | 8 |

TABLE 3-continued

| | | Example | | | | | | |
|---|---|---|---|---|---|---|---|---|
| | | 22 | 23 | 24 | 25 | 26 | 27 | 28 |
| (A-1) | Sodium carbonate | 5.05 | 5.05 | 4.05 | 5.05 | 1.05 | 5.27 | 4.60 |
| | Sodium hydrogen carbonate | | | | | | | |
| (A-2) *4 | Copper sulfate pentahydrate | 0.20 (0.13) | 0.20 (0.13) | 0.20 (0.13) | 0.20 (0.13) | 0.20 (0.13) | 0.20 (0.13) | 0.20 (0.13) |
| | Copper chloride dihydrate | | | | | | | |
| | Copper glycine | | | | | | | |
| (A-3) *5 | MGDA | | | 2.50 (2.00) | 2.50 (2.00) | 2.50 (2.00) | 2.50 (2.00) | 2.50 (2.00) |
| | NTA | | | | | | | |
| | GLDA | | | | | | | |
| | IDS | 2.50 (2.00) | | | | | | |
| | HIDA | | 2.50 (2.50) | | | | | |
| (A-4) | $C_{13}$—O—$(EO)_9(PO)_2$—H | 0.25 | 0.25 | | | 0.25 | 0.03 | 0.70 |
| | $C_{palm}$—O—$(EO)_7(PO)_2$—H | | | 0.25 | | | | |
| | $C_{13}$—O—$(EO)_5(PO)_1$—H | | | | 0.25 | | | |
| (B-2) | Sodium percarbonate | 92.00 | 92.00 | 92.00 | 92.00 | 95.00 | 92.00 | 92.00 |
| | (in the content of sodium carbonate) | (62.10) (29.90) | (62.10) (29.90) | (62.10) (29.90) | (62.10) (29.90) | (64.13) (30.87) | (62.10) (29.90) | (62.10) (29.90) |
| | (in the content of hydrogen peroxide) | | | | | | | |
| Optional component | Sodium sulfate | | | | 1.00 | | | |
| Total | | 100 | 100 | 100 | 100 | 100 | 100 | 100 |
| (A-3)/(A-2) molar ratio | | 7.4 | 14.1 | 9.2 | 9.2 | 9.2 | 9.2 | 9.2 |
| Evaluation | Foam volume (mL) | 5 | 5 | 3 | 2 | 5 | 2 | 9 |
| | Disinfecting power test | A | B | A | A | B | A | A |
| | Hydrogen peroxide residual ratio | B | A | A | A | A | A | A |
| | Actual machine disinfection test (number of residual bacteria) | 7 | 8 | 4 | 5 | 5 | 9 | 4 |

TABLE 4

| | | Comparative Example | | | | | | | | |
|---|---|---|---|---|---|---|---|---|---|---|
| | | 11 | 12 | 13 | 14 | 15 | 16 | 17 | 18 | 19 |
| (A-1) | Sodium carbonate | 5.25 | 7.55 | 5.30 | 97.05 | 1.95 | 5.45 | 3.75 | 3.75 | 3.75 |
| | Sodium hydrogen carbonate | | | | | | | | | |
| (A-2) *4 | Copper sulfate pentahydrate | | 0.20 (0.13) | 0.20 (0.13) | 0.20 (0.13) | 0.20 (0.13) | 0.50 (0.32) | 0.50 (0.32) | 0.50 (0.32) | 0.50 (0.32) |
| | Copper chloride dihydrate | | | | | | | | | |
| | Copper glycine | | | | | | | | | |
| (A-3) *5 | MGDA | 2.50 (2.00) | | 2.50 (2.00) | 2.50 (2.00) | 5.60 (4.48) | 1.80 (1.44) | 3.50 (2.80) | 3.50 (2.80) | 3.50 (2.80) |
| (A-4) | $C_{13}$—O—$(EO)_9(PO)_2$—H | 0.25 | 0.25 | | 0.25 | 0.25 | 0.25 | | | |
| | $C_{palm}$—O—$(EO)_7(PO)_2$—H | | | | | | | | | |
| | $C_{13}$—O—$(EO)_5(PO)_1$—H | | | | | | | | | |
| (A-4') | $C_{12,14}$—O—$(EO)_3(PO)_3$—H | | | | | | | 0.25 | | |
| | $C_{13}$—O—$(EO)_7(PO)_3$—H | | | | | | | | 0.25 | |
| | $C_{12,14}$—O—$(EO)_{15}$—H | | | | | | | | | 0.25 |
| (B-2) | Sodium percarbonate | 92.00 | 92.00 | 92.00 | | 92.00 | 92.00 | 92.00 | 92.00 | 92.00 |
| | (in the content of sodium carbonate) | (62.10) | (62.10) | (62.10) | | (62.10) | (62.10) | (62.10) | (62.10) | (62.10) |
| | (in the content of hydrogen peroxide) | (29.90) | (29.90) | (29.90) | | (29.90) | (29.90) | (29.90) | (29.90) | (29.90) |
| Optional component | Sodium sulfate | | | | | | | | | |
| Total | | 100 | 100 | 100 | 100 | 100 | 100 | 100 | 100 | 100 |
| (A-3)/(A-2) molar ratio | | — | 0.0 | 9.2 | 9.2 | 20.6 | 2.7 | 5.2 | 5.2 | 5.2 |
| Evaluation | Foam volume (mL) | 5 | 5 | 1 | 5 | 5 | 5 | 1 | 2 | 36 |
| | Disinfecting power test | D | A | C | D | C | A | C | C | A |
| | Hydrogen peroxide residual ratio | A | D | A | — | A | D | A | A | A |
| | Actual machine disinfection test (number of residual bacteria) | 168 | 88 | 72 | 1665 | 116 | 59 | 27 | 35 | — |

*4: In Table 3 and Table 4, the number in the parentheses for the component (A-2) represents the amount in terms of anhydride.
*5: In Table 3 and Table 4, the number in the parentheses for the component (A-3) represents the amount in terms of the pure component.

As shown in Tables 3 and 4, Examples 15 to 28 all had a foam volume of 10 mL or less, and satisfactory results were obtained in all the evaluations of the initial disinfecting power evaluation, the hydrogen peroxide persistence evaluation and the actual machine disinfection test.

On the other hand, in Comparative Example 11 in which the component (A-2) was not incorporated, Comparative Example 13 in which the component (A-4) was not incorporated, Comparative Example 14 in which the component (B-2) was not incorporated, and Comparative Example 15 in which the molar ratio of the mixing ratio of the mixing amount of (A-3)/mixing amount of (A-2) was 20.6, the evaluation results for the initial disinfecting power evaluation and the actual machine disinfection test were all poor.

In Comparative Example 12 in which the component (A-3) was not incorporated, and Comparative Example 16 in which the molar ratio of the mixing amount of (A-3)/mixing amount of (A-2) was 2.7, the results of the hydrogen peroxide persistence evaluation and the actual machine disinfection test were poor. It is speculated that the actual machine disinfection test results were poor because hydrogen peroxide was degraded in a short time in the washing machine for bottles.

In Comparative Examples 17 and 18 in which $C_{12,14}$—O-$(EO)_3(PO)_3$—H or $C_{13}$—O-$(EO)_7(PO)_3$—H was incorporated instead of the component (A-4), the initial disinfecting power evaluation results and the actual machine disinfection test results were all poor.

In Comparative Example 19 in which $C_{12,14}$-$(EO)_{15}$—H was incorporated instead of the component (A-4), the foaming power was high, and when the disinfectant composition was supplied to the washing in a bottle washing machine in the actual machine disinfection test, foam overflow from the washing machine occurred, while rinsability was also poor.

INDUSTRIAL APPLICABILITY

According to the present invention, disinfectant compositions for hard articles which have high disinfecting power against the surfaces of hard articles, have satisfactory stability of hydrogen peroxide in water, and have low foaming tendency, and a method for disinfecting the surface of a hard article by using the disinfectant composition for hard articles, can be provided.

We claim:

1. A disinfectant composition for hard articles used for disinfection of the surfaces of hard articles comprising:
   a two-agent type disinfectant composition including a first agent containing a powder mixture (A) and a second agent containing an aqueous hydrogen peroxide solution (B-1) wherein (B-1) comprises hydrogen peroxide in a concentration of 30-65 mass %,
   wherein the powder mixture (A) contains 80-98 mass % of an alkali metal salt (A-1) exhibiting basicity when the salt is in a form of an aqueous solution, 0.1-0.5 mass % of a water-soluble copper salt (A-2), 0.5-5 mass % of a compound (A-3) represented by the following formula (1), and 0.05-1.6 mass % of a nonionic surfactant (A-4) represented by the following formula (2),
   wherein a molar ratio of the water-soluble copper salt (A-2) and the compound (A-3) represented by a mixing amount of (A-3)/mixing amount of (A-2) is 3.0 to 20:

[Chemical Formula 1]

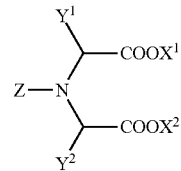

(1)

wherein $Y^1$ and $Y^2$ each independently represent a hydrogen atom, an alkyl group having 1 to 3 carbon atoms, —$CH_2$—$COOX^3$, —$CH(OH)$—$COOX^4$, —$CH_2CH_2$—$COOX^5$, —$CH_2CH_2$—OH or $CH_2$—OH; Z represents a hydrogen atom, an alkyl group having 8 to 16 carbon atoms, —$CH_2$—$COOX^6$ or $CH_2CH_2$—OH; $X^1$ to $X^6$ each independently represent a hydrogen atom, an alkali metal atom, an alkaline earth metal atom, or a cationic ammonium group;

[Chemical Formula 2]

$$R^1O(EO)_p(PO)_qH \quad (2)$$

wherein $R^1$ represents an alkyl group or alkenyl group having 8 to 20 carbon atoms; EO represents an oxyethylene group; PO represents an oxypropylene group; p represents the average number of added moles of EO and is a number of 2 to 10; q represents the average number of added moles of PO and is a number of 1 to 2; and p>q.

2. A disinfectant composition for hard articles used for the disinfection of the surfaces of hard articles comprising:
   a single-agent type disinfectant composition including an alkali metal salt (A-1) that exhibits basicity when the salt is in a form of an aqueous solution, 0.1-0.4 mass % of a water-soluble copper salt (A-2), 0.9-4.5 mass % of a compound (A-3) represented by the following formula (1), 0.07-0.7 mass % of a nonionic surfactant (A-4) represented by the following formula (2), and 80-95 mass % of an inorganic peroxide (B-2) that releases hydrogen peroxide in water, wherein a molar ratio of the water-soluble copper salt (A-2) and the compound (A-3) represented by a mixing amount of (A-3)/mixing amount of (A-2) is 3.0 to 20:

[Chemical Formula 3]

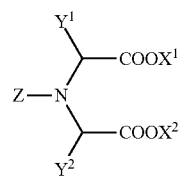

(1)

wherein $Y^1$ and $Y^2$ each independently represent a hydrogen atom, an alkyl group having 1 to 3 carbon atoms, —$CH_2$—$COOX^3$, —$CH(OH)$—$COOX^4$, —$CH_2CH_2$—$COOX^5$, —$CH_2CH_2$—OH or $CH_2$—OH; Z represents a hydrogen atom, an alkyl group having 8 to 16 carbon atoms, —$CH_2$—$COOX^6$ or $CH_2CH_2$—OH; $X^1$ to $X^6$ each independently represent a hydrogen atom, an alkali metal atom, an alkaline earth metal atom, or a cationic ammonium group;

[Chemical Formula 2]

(2)

wherein $R^1$ represents an alkyl group or alkenyl group having 8 to 20 carbon atoms; EO represents an oxyethylene group; PO represents an oxypropylene group; p represents the average number of added moles of EO and is a number of 2 to 10; q represents the average number of added moles of PO and is a number of 1 to 2; and p>q.

3. A method for disinfecting the surface of a hard article by using the disinfectant composition for hard articles according to claim 1, the method comprising:
- diluting a first agent containing the powder mixture (A) and thereby obtaining a dilution;
- mixing the dilution with a second agent containing the aqueous hydrogen peroxide solution (B-1), and thereby obtaining a liquid mixture; and
- bringing a surface of a hard article into contact with the liquid mixture.

4. A method for disinfecting a surface of a hard article by using the disinfectant composition for hard articles according to claim 2, the method comprising:
- diluting the disinfectant composition for hard articles with water, and thereby obtaining a dilution; and
- bringing a surface of a hard article into contact with the dilution.

5. The method according to claim 3, wherein the hard article is a food packaging container.

6. The method according to claim 4, wherein the hard article is a food packaging container.

7. The method according to claim 3, wherein the material that constitutes a surface of the hard article is glass, polycarbonate, or polyethylene terephthalate.

8. The method according to claim 4, wherein the material that constitutes a surface of the hard article is glass, polycarbonate, or polyethylene terephthalate.

9. The method according to claim 5, wherein the material that constitutes a surface of the hard article is glass, polycarbonate, or polyethylene terephthalate.

* * * * *